United States Patent [19]

Drinkard

[11] 4,241,230
[45] Dec. 23, 1980

[54] CONTROL SYSTEM FOR THE SELECTIVE HYDROGENATION OF ACETYLENE PRESENT IN ETHYLENE PRODUCT STREAMS

[75] Inventor: B. M. Drinkard, Beaumont, Tex.

[73] Assignee: Mobil Oil Corporation, New York, N.Y.

[21] Appl. No.: 95,825

[22] Filed: Nov. 19, 1979

[51] Int. Cl.³ .......................... C07C 5/03; C07C 5/08
[52] U.S. Cl. ................................. 585/259; 422/62; 422/108; 422/110; 585/263
[58] Field of Search .................. 585/259, 263; 422/62, 422/108, 110

[56] References Cited

U.S. PATENT DOCUMENTS

| | | | |
|---|---|---|---|
| 2,802,889 | 8/1957 | Frevel et al. | 585/262 |
| 2,814,653 | 11/1957 | Hogan et al. | 585/259 |
| 3,113,980 | 12/1963 | Robinson | 585/260 |
| 3,153,679 | 10/1964 | Rottmayr | 585/259 |
| 3,471,582 | 10/1969 | Lupfer | 585/263 |
| 3,656,911 | 4/1972 | Hobbs | 585/500 |
| 3,972,804 | 8/1976 | McLaughlin et al. | 422/110 |

*Primary Examiner*—Curtis R. Davis
*Attorney, Agent, or Firm*—Charles A. Huggett; Charles J. Speciale

[57] ABSTRACT

Acetylene contained in an ethylene product stream in minor amounts is selectively hydrogenated to ethylene in the presence of suitable catalysts in a two stage converter having a primary reactor stage providing hydrogenation of a portion of the acetylene present in the stream in series with a secondary reactor stage providing hydrogenation of substantially all of the remaining unreacted acetylene. Overall process control is achieved by adjusting the molar ratio of hydrogen to acetylene in the feed stream for the primary reactor stage in response to feedforward information from an analyzer for the primary stage feed stream and feedback information from an analyzer for the primary stage effluent stream to provide a primary stage effluent of substantially constant acetylene content. The substantially constant acetylene content of the primary reactor stage effluent allows operation of the secondary reactor stage to be optimized to provide for maximum ethylene recovery and a secondary stage stream effluent having a level of acetylene therein within desired process specifications.

18 Claims, 1 Drawing Figure

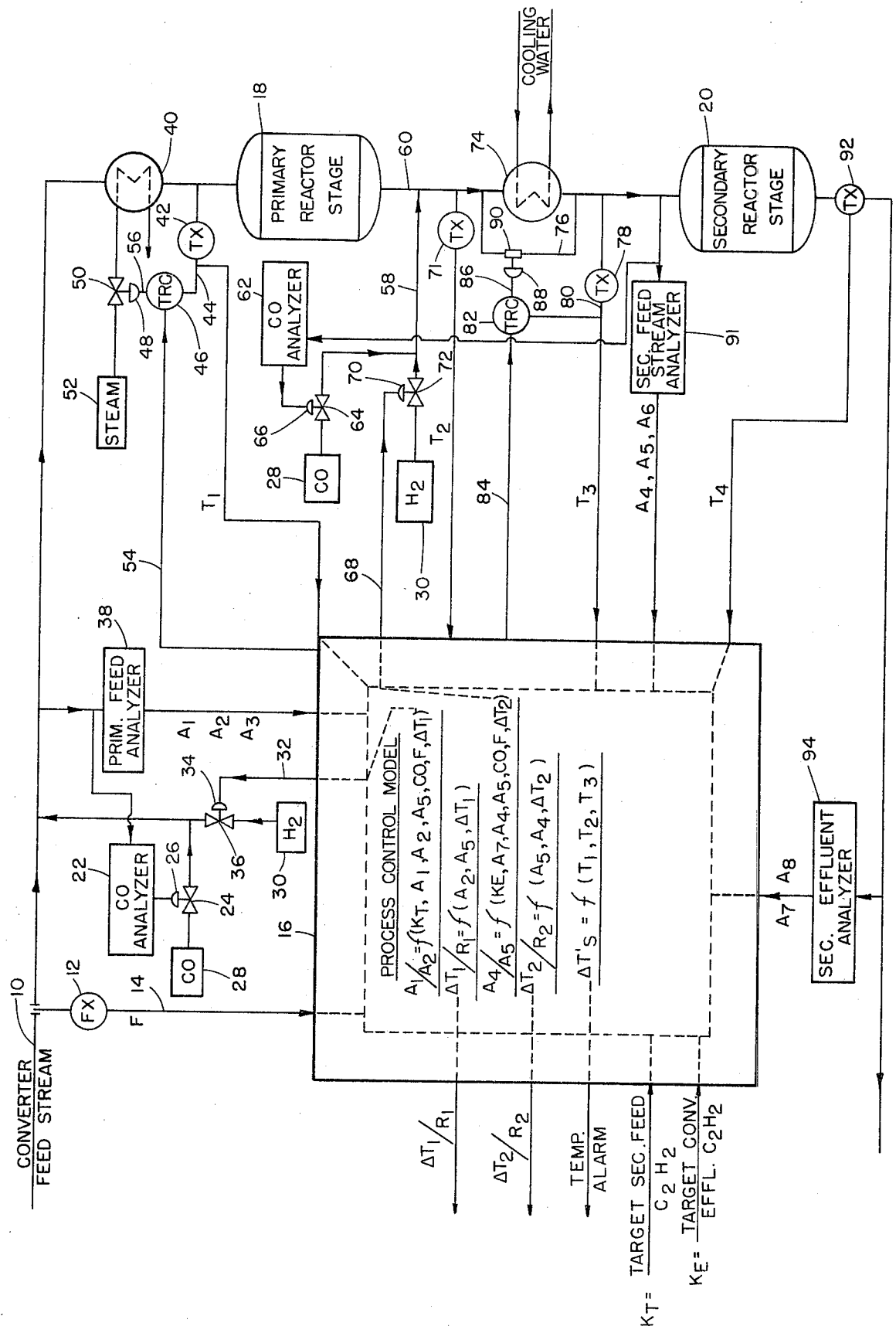

CONTROL SYSTEM FOR THE SELECTIVE HYDROGENATION OF ACETYLENE PRESENT IN ETHYLENE PRODUCT STREAMS

BACKGROUND OF THE INVENTION

1. Field of the Invention

The present invention relates in general to a process for the selective hydrogenation of acetylene present in an ethylene product stream, and more particularly pertains to a control system for such a process which optimizes the conversion of acetylene to ethylene with a minimum consumption of hydrogen. As used herein, the term "acetylene" includes the hydrocarbon $C_2H_2$ as well as other acetylenic hydrocarbons, and the term "ethylene product stream" includes streams containing the hydrocarbon $C_2H_4$ as well as streams containing other mono- and diolefinically unsaturated hydrocarbons.

It would be desirable to have a system and process for the accurate and controlled hydrogenation of acetylene in an ethylene product stream for both economic and operational benefits including, provision of a more consistent product quality, reduction in the amount of ethylene hydrogenated to ethane in the acetylene reactor, elimination of ethylene production loss due to acetylene reactor shut-down required by process upsets, extension of the life of catalysts by elimination of reactor runaways, and reduction of the amount of time an operator must spend attending to achievement of a tighter control over the process, increase in run time between regeneration of catalyst by reduced formation of heavy hydrocarbon poisons, and reduction of hydrogen consumption.

2. Description of the Prior Art

The catalyzed selective hydrogenation of acetylene to ethylene is a well known industrial process (see for example U.S. Pat. Nos. 2,802,889; 2,814,653; and 3,113,980). Ethylene product streams are usually contaminated with small amounts of acetylene which must be removed at least to the level of a few parts per million for the stream to meet process requirements, for example, in polymerization processes or to avoid formation of explosive acetylides in equipment. The conversion of minor concentrations of acetylene to ethylene in ethylene product streams is conventionally carried out by hydrogenating the acetylene in the presence of a suitable hydrogenation catalyst. Ideally, substantially all of the acetylene should be hydrogenated to ethylene without resulting in any appreciable hydrogenation of ethylene to ethane and/or ethylene polymerization to form "green-oil", and an excessive consumption of hydrogen. In practice this has been difficult to accomplish. Generally, ethylene plant acetylene converters are operated with a view toward maintaining an overconversion reaction to prevent acetylene "leakage" as this reduces the likelihood of producing off-specification ethylene. However, over-conversion has the disadvantage of increasing the hydrogenation of ethylene to ethane thereby reducing the recovery of ethylene and increasing the consumption of hydrogen. Polymerization of ethylene results in further loss of ethylene and produces a "green-oil" type hydrocarbon material that accelerates deactivation of the catalyst. Attempts have therefore been made to optimize or precisely control the selective hydrogenation of acetylene present in ethylene streams to maximize ethylene recovery and minimize hydrogen consumption.

U.S. Pat. No. 3,471,582 describes a control system for the selective hydrogenation of acetylenic components of an olefin/diolefin stream in a series of hydrogenation reactors which is based upon control of hydrogenation reaction temperature. In accordance with this control system, the temperature within the hydrogenation reaction zone is controlled by manipulating the reactant feed temperature between the product and reactant streams to thereby maintain a predetermined difference in temperature. When the product temperature reaches a predetermined maximum, control of the reactant feed temperature is automatically switched to be responsive solely to the product stream temperature. Control in this manner continues until the product temperature falls below the predetermined maximum, at which time control of the reactant feed temperature is automatically switched to be responsive to the difference in temperature between the product and reactant streams. Similarly, U.S. Pat. No. 3,656,911 provides a selective hydrogenation control system for a series of hydrogenation reactors in which the temperatures of the feed streams introduced into the reactors are controlled in response to temperature and flow measurements and analyses of the feed and effluent streams. U.S. Pat. No. 3,839,483 describes a control system for a single hydrogenation reactor in which the ratio of hydrogen to acetylene in the feed to the reactor is adjusted in response to the concentration of acetylene and hydrogen in the reactor effluent, and the temperature of the feed to the reactor is adjusted responsive to the hydrogen concentration in the reactor effluent.

SUMMARY OF THE INVENTION

The present invention contemplates the provision of an improved method and system for operating an acetylene converter for an ethylene plant in which excessive amounts of acetylene in the ethylene product stream are converted to ethylene by catalytic hydrogenation carried out in a two-stage reactor having primary and secondary stages. Pursuant to the teachings herein, operation of the secondary stage of the reactor is optimized to produce a concentration of acetylene in the effluent product thereof within product specifications while minimizing undesirable hydrogenation of ethylene to ethane. This is accomplished by providing a feed stream for the secondary reactor stage having a relatively constant acetylene concentration, which requires operation of the primary reactor stage to provide an effluent output stream having the desired acetylene concentration. Operation of the primary reactor stage is controlled by adjusting the molar ratio of hydrogen to acetylene in the feed stream thereto in response to feedback information from a primary stage effluent stream analyzer providing an analysis of the concentration of acetylene therein, and feedforward information from a process analyzer providing analyses of the hydrogen and acetylene concentrations in the converter feed stream and a transducer measuring the flow rate of the converter feed stream. Furthermore the molar ratio of hydrogen to acetylene in the feed stream for the primary reactor stage is controlled by the selective addition of hydrogen to that stream through a control feed stream coupled thereto. Operation of the secondary reactor stage is also controlled by adjusting the molar ratio of hydrogen to acetylene in its feed stream. More particularly, operation of the secondary reactor stage is controlled by selective addition of hydrogen to its feed stream through a control stream coupled thereto. Furthermore the secondary reactor stage is controlled in response to feedback information from an analyzer for the secondary stage effluent stream indicating the concentration therein of acetylene, and feedforward information from an analyzer for the secondary reactor stage feed stream indicating the concentrations therein of hydrogen and acetylene.

Moreover in the disclosed embodiment, the temperatures are sensed in the feed stream to the primary reactor stage, the feed stream to the secondary reactor stage, and the effluent stream of the secondary reactor stage. These temperature measurements allow the temperature differentials across each of the primary and secondary reactor stages to be monitored to detect a potential onset in either stage of a thermal runaway caused by excessive conversion therein of ethylene to ethane. Detection of the onset of a thermal runaway can be utilized to activate an alarm and/or initiate emergency control action to prevent a possible unsafe converter operation. Also the concentration of carbon monoxide in the feed stream to each of the primary and secondary reactor stages is measured, and carbon monoxide is selectively added to each control stream in response to the measurement to maintain the carbon monoxide concentration therein at a level to provide for optimum reactivity/selectivity of the catalyst. Also the feed streams to both the primary and secondary reactor stages are passed through heat exchangers to selectively control the temperature of each stream.

Accordingly, it is a primary object of the present invention to provide for the operation of an acetylene converter for an ethylene plant in which excessive amounts of acetylene in the ethylene product stream are converted to ethylene, while the amount of ethylene converted to ethane is minimized.

It is a further object of the present invention to provide a system and process for the controlled hydrogenation of acetylene in an ethylene product stream so as to result in a more consistent product quality, a reduction in the amount of ethylene hydrogenated to ethane, and ethylene polymerization to "green-oil", an elimination of ethylene production loss due to acetylene converter shutdown, an extension of the life of catalysts in the converter by elimination of reactor runaway, and a reduction of the amount of time required by an operator to achieve adequate control over the operation.

BRIEF DESCRIPTION OF THE DRAWING

The foregoing and other objects and advantages of the inventive method and system for operating an acetylene converter constructed pursuant to the teachings of the present invention may be more readily understood by one skilled in the art, having reference to the following detailed description of a preferred embodiment taken in conjunction with the accompanying drawing which illustrates the converter flow streams through the primary and secondary reactor stages, the control measurements taken of the various streams and the parameters of the system and process controlling various functions in the converter.

DETAILED DESCRIPTION OF THE DRAWING

Referring now in detail to the drawing, the effluent product stream from an ethylene plant, which consists mainly of ethylene with minor amounts of acetylene and other impurities therein, flows through a conduit 10 as an imput feed stream for a two-stage acetylene converter. A suitable transducer 12 in the converter feed stream measures the flow rate of the stream, and produces an output signal indicative thereof on line 14 which is directed to a process control system 16. The rate-of-flow transducer 12 may be of a known type wherein a pressure drop across a diaphragm orifice is measured by a differential pressure transducer.

Initially, it should be mentioned that in the illustrated embodiment several parameters in the disclosed process and system are maintained relatively constant during normal operation, but may be adjusted on command. These parameters include the temperatures of the reactor feed streams to both the primary and secondary reactor stages 18 and 20, and the carbon monoxide (CO) concentrations in the control feed streams to both the primary and secondary stages.

In the accompanying drawing, the legends set forth below refer to the following process variables:

$A_1$ = the concentration of $H_2$ in the primary feed stream $A_2$ = the concentration of $C_2H_2$ in the primary feed stream $A_3$ = the concentration of $C_2H_4$ in the primary feed stream $A_4$ = the concentration of $H_2$ in the secondary feed stream $A_5$ = the concentration of $C_2H_2$ in the secondary feed stream $A_6$ = the concentration of $C_2H_4$ in the secondary feed stream $A_7$ = the concentration of $C_2H_2$ in the secondary effluent stream $A_8$ = the concentration of $C_2H_4$ in the secondary effluent stream F = the feed rate in the primary feed stream $\Delta T_1$ = the temperature differential across the primary reactor $\Delta T_2$ = the temperature differential across the secondary reactor $R_1$ = the rate of conversion of $C_2H_2$ in the primary reactor $R_2$ = the rate of conversion of $C_2H_2$ in the secondary reactor $K_T$ = the target concentration of $C_2H_2$ in the secondary feed stream $K_E$ = the target concentration of $C_2H_2$ in the effluent stream.

Further, in accompanying drawing, the control system implements broadly the following process control model, within the context of the specific teachings herein:

$$A_1/A_2 = f(K_T, A_1, A_2, A_5, CO, F, T_1)$$

$$\Delta T_1/R_1 = f(A_2, A_5, \Delta T_1)$$

$$A_4/A_5 = f(K_e, A_7, A_4, A_5, CO, F, \Delta T_2)$$

$$\Delta T_2/R_2 = f(A_5, A_4, \Delta T_2)$$

$$\Delta T's = f(T_1, T_2, T_3, T_4)$$

A carbon monoxide analyzer 22 measures the concentration of carbon monoxide in the feed stream for the primary reactor stage, and in response thereto activates an adjustable control valve 24 via a valve controller 26. Accordingly, carbon monoxide is selectively introduced into the control feed stream from a source 28 to maintain the concentration of carbon monoxide therein at a level for efficient operation of the primary reactor. The same control feed stream carrying carbon monoxide to the converter feed stream also introduces hydrogen thereto from a source 30 under the direction of a control system which will be described in greater detail below. The output of the control system on line 32 is directed to a valve controller 34, which in turn controls the position of an adjustable control valve 36 to regulate the quantity of hydrogen passing therethrough to the converter feed stream.

A primary feed stream analyzer 38, which may be a chromatographic instrument, provides an analysis of the content of the feed stream for hydrogen ($H_2$) acetylene ($C_2H_2$) and ethylene ($C_2H_4$), and this information is directed to the process control system 16.

The feed stream then flows through a heat exchanger 40, wherein steam is utilized as the exchange medium, to increase its temperature under the control of a set temperature control system. An appropriate transducer 42, which may be a thermocouple, measures the temperature of the feed stream after its passage through the heat exchanger 40, and produces an output signal T, representative thereof. The transducer output signal is directed to a temperature recording controller (TRC) 46 which selectively actuates a valve controller 48 for an adjustable control valve 50 to regulate the flow of steam from a suitable source 52 to the heat exchanger. The temperature controller can be any suitable type of controller known in the art having a set point input signal, a measurement signal input, and a control output signal which is directed to a valve controller for suitable controlled operation thereof. In the temperature controller, the input signal on line 44 from the temperature transducer is compared with the set point input signal on line 54 from the process control system, and an output signal is produced on line 56 proportional to the difference between the two input signals. The controller 46 also produces a printed record of temperature as a function of time, such that a permanent record is maintained of the temperature of the stream at that point. The output of the temperature transducer is also directed to the process control system for reasons explained in greater detail below.

The feed stream then flows through the primary reactor stage wherein acetylene is converted to ethylene by catalytic hydrogenation thereof. A control feed stream 58 for the secondary reactor stage then joins the effluent output stream 60 of the primary reactor stage.

An arrangement is utilized for the input feed stream for the secondary reactor stage which is similar to the arrangement at the input to the primary reactor stage. A carbon monoxide analyzer 62 measures the concentration of carbon monoxide in the secondary feed stream for the secondary reactor stage, and in response thereto controls an adjustable control valve 64 via a valve controller 66. This results in carbon monoxide from a source 28 being selectively introduced into the secondary control feed stream to maintain the concentration thereof in feed stream for optimum performance of the secondary reactor. The secondary control feed stream also introduces hydrogen from a source 30 to the feed stream for the secondary reactor stage in a manner similar to that for the primary reactor stage. An output of the control system on line 68 is directed to a valve controller 70 which in turn controls the position of an adjustable control valve 72 to regulate the amount of hydrogen passing therethrough to the secondary stage feed stream. An appropriate transducer 71, which may be a termocouple, measures the temperature of the effluent stream of the primary reactor stage, and provides an output signal $T_2$ representative thereof. The feed stream for the secondary reactor stage then flows through a heat exchanger 74, wherein water is utilized as the heat exchanger medium, to heat or cool the temperature of the stream under the control of a set temperature control system. A portion of the effluent stream flows through a bypass conduit 76 around the heat exchanger 74, and the amount of the stream bypassing the heat exchanger is regulated by a control valve 90, which is in turn controlled by a set temperature control system. In this system an appropriate temperature transducer 78, which may be a thermocouple, measures the temperature of the effluent downstream of the heat exchanger 74 and a bypass conduit 76 around the heat exchanger, and produces an output signal $T_3$ on line 80 representative thereof. This output signal is directed to a temperature recording controller 82 which compares it with a set point input signal on line 84 from the process control system, and produces an output signal on line 86 proportional to the difference in the input signals. Its output signal is directed to a valve controller 88 which selectively actuates an adjustable control valve 90 to regulate the flow of the stream through the bypass conduit 76 around the heat exchanger. In this manner control is maintained over the temperature of the feed stream for the secondary reactor stage. The controller 82 also produces a printed record of temperature as a function of time, such that a permanent record is maintained of the temperature of the stream at that point. The output from the temperature transducer 78 is also directed to the process control system for operation therein as explained in greater detail below.

A secondary feed stream analyzer 91, which may be a chromatographic instrument, provides an analysis of the content of that feed stream for hydrogen ($H_2$) acetylene ($C_2H_2$) and ethylene ($C_2H_4$), and this information is directed to the process control system 16.

The feed stream then flows through the secondary reactor stage wherein substantially all of the remaining acetylene therein is converted by catalytic hydrogenation to ethylene to within process specifications (e.g., 0.5–1.0 ppm). A temperature transducer 92 at the output of the secondary reactor stage measures the temperature of the effluent stream, produces an output signal $T_4$ indicative thereof, and directs it to the process controller 16.

The output effluent stream from the secondary reactor stage is analyzed in a secondary effluent stream analyzer 94, which may also be a chromatographic instrument, to determine the content of the effluent stream with regard to concentrations of acetylene and ethylene.

In the disclosed embodiment, hydrogen is selectively added to the feed stream for the primary reactor stage to control the molar ratio of hydrogen to acetylene in that stream. That control function is accomplished as follows. The primary feed stream analyzer 38 produces outputs indicative of the concentrations therein of hydrogen and acetylene. The secondary feed stream analyzer 91 produces an output signal indicative of the concentration of acetylene in that stream, and that signal is compared in the process control system 16 with a signal representing the known target or desired concentration of acetylene for the secondary feed stream. If the measured concentration of acetylene in the secondary stage feed stream is greater than the target concentration, the molar ratio of hydrogen to acetylene in the primary stage feed stream may be increased to bring the acetylene concentration in the secondary feed stream to the target concentration. Likewise, if the measured concentration of acetylene in the secondary stage feed stream is less than the target concentration, the molar ratio of hydrogen to acetylene in the primary stage feed stream is decreased to bring the acetylene concentration in the secondary stage feed stream to its target concentration. The carbon monoxide concentration in the primary feed stream is maintained at a level to provide for optimum reactivity selectivity reaction state for the catalyst (CO concentration being reduced as a function of stream days to maintain catalyst activity). The temperature differential across the primary reactor stage, as measured by the first and second temperature transducers 42 and 78 is also monitored to detect the potential onset of a thermal runaway caused by excessive hydrogenation of ethylene to ethane in the first reactor stage. If this temperature differential becomes too great, the hydrogenation reaction in the primary reactor stage may be controlled by readjusting downwardly the molar ratio of hydrogen to acetylene in the primary reactor feed stream to reduce the possibility of a thermal runaway. Accordingly, hydrogen is selectively added to the feed stream for the primary reactor stage in a manner so as to control the molar ratio of hydrogen to acetylene in the primary stage feed stream. That molar ratio is controlled as a function of the target concentration of acetylene in the effluent stream of the primary stage, the measured concentration of acetylene in the primary stage effluent stream, the measured concentrations of hydrogen and acetylene in the primary stage feed stream, and the temperature differential across the primary reactor stage.

The control system produces an output signal indicative of the temperature differential across the primary reactor stage as a ratio of the conversion rate ($C_2H_2R_x$) of the acetylene therein, which conversion rate is determined by comparing the output of the primary feed stream analyzer for concentration of acetylene with the output of the secondary feed stream analyzer for its output of acetylene concentration while taking into account the flow rate of the stream as measured by transducer 12.

Hydrogen is also selectively added to the feed stream for the secondary reactor stage to control the molar ratio of hydrogen to acetylene in that stream. That control function is accomplished as follows. The secondary stage effluent stream analyzer 94 produces an output signal indicative of the concentration of acetylene in that stream, and that signal is compared in the process control system 16 with a signal representing the desired concentration of acetylene for that stream, depending upon the product specifications. If the measured concentration of acetylene in the secondary stage effluent stream is greater than the target concentration, the molar ratio of hydrogen to acetylene in the secondary stage feed stream may be increased to bring the acetylene concentration in the secondary effluent stream to the target process specifications. Likewise if the measured concentration of acetylene is less than the target concentration, the molar ratio of hydrogen to acetylene in the secondary stage feed stream may be decreased to bring the acetylene concentration in the secondary effluent stream to the target process specifications. Also carbon monoxide is added to the secondary feed stream to maintain optimum activity/reactivity state for the catalyst (generally CO concentration will decrease with catalyst age since regeneration). The temperature differential across the secondary reactor stage, as measured by the temperature transducers 78 and 92, is also monitored to detect the potential onset of a thermal runaway caused by excessive hydrogenation of ethylene to ethane and/or polymerization of ethylene in the secondary reactor stage. If this temperature differential becomes too great, the hydrogenation reaction in the secondary reactor stage may be controlled by readjusting downwardly the molar ratio of hydrogen to acetylene in the secondary reactor feed stream, to reduce the possibility of a thermal runaway. Accordingly, hydrogen is selectively added to the feed stream for the secondary reactor stage in a manner so as to control the molar ratio of hydrogen to acetylene in the secondary stage feed stream. That molar ratio is controlled as a function of the target concentration of acetylene in the effluent stream of the secondary stage, the measured concentration of acetylene in the secondary stage effluent stream, the measured concentrations of hydrogen and acetylene in the secondary stage feed stream, and the temperature differential across the secondary reactor stage.

The control system also produces an output signal indicative of the temperature differential across the secondary reactor stage as a ratio to the conversion rate ($C_2H_2R_x$) of acetylene therein, which conversion rate is determined by comparing the output of the secondary feed stream analyzer for concentration of acetylene and the output of the secondary effluent stream analyzer for its output of acetylene concentration while taking into account the flow rate through the converter as measured by transducer 12.

Further, the control system produces a temperature alarm signal in which the temperature differentials between $T_1$ and $T_2$, and $T_3$ and $T_4$ are constantly monitored, and any abnormal difference indicating a potential thermal runaway in the reactor is utilized to trigger an alarm signal.

By way of a specific example, the acetylene converter described with particularity herein is known as a "back-end" converter since the converter feed stream has been subjected to hydrogen removal (deethanizer overhead feeds the converter). In the particular converter described herein the composition of the converter feed stream and the normally expected variation of each constituent is as follows.

| Component | Mol % Typical | Mol % Range |
| --- | --- | --- |
| Hydrogen | *1.5 | 0.7–2.0 |
| Methane | *0.1 | 0.05–0.15 |
| Ethylene | 70.5 | 67.0–72.5 |
| Ethane | 26.9 | 25.0–32.0 |
| Acetylene | 1.0 | 0.7–1.6 |
| $C_3$ & heavier | 0.1 | 0.05–0.3 |

*substantially nil before hydrogen addition.

Further the primary and secondary feed $H_2/C_2$ = ratios are as follows.

| | *Range of $H_2/C_2$ = ratios (molar) |
| --- | --- |
| Primary Converter | 1.0–1.5 |

| *Range of H₂/ C₂ ≡ ratios (molar) |
|---|
| -continued |
| Secondary Converter 1.5–2.0 |

*$H_2/C_2 \equiv$ will increase with deactivation of catalyst.

In the described acetylene converter, the carbon monoxide in the reactor feeds is monitored and controlled as a function of activity/selectivity (time on oil, inlet temperature, ΔT across reactor, etc). The carbon monoxide function as a "selective poison". Those catalyst sites that promote the undesired reactions (hydrogenation of ethylene to ethane and ethylene polymerization) are deactivated or tempered to a much greater extent than those sites promoting the hydrogenation of acetylene to ethylene. Consequently, there are three noteworthy effects: (1) selectivity and ethylene recovery are improved; (2) by reducing the formation of "green-oil" material, run life between regenerations is improved since this heavy material causes rapid catalyst deactivation; and (3) hydrogen consumption is reduced.

Also in an equilibrated reaction a portion of the carbon monoxide entering the reactor will "leak" therethrough. If "leakage" of carbon monoxide from the primary into the secondary reactor is greater than secondary reactor requirement, carbon monoxide poisoning will result in nonoptimized performance of the secondary reactor and a serious loss of catalyst activity. This fact substantially imposes a reactor "line-up" that locates the reactor with the greatest carbon monoxide requirement in the secondary position.

In practice, the target acetylene concentration in the secondary reactor feed is set as a percentage of the acetylene in the primary reactor feed; with an acceptable range being 5–50%. The particular target depends on how efficiently the primary reactor is performing (ethylene recovery, maximum reactor temperature, ΔT, etc.) accordingly total converter economics must be considered. Once the target for the secondary feed acetylene concentration is selected, the primary reactor is operated to maintain this target to provide for optimum performance in the secondary reactor.

The control over the quantity of hydrogen added to the feed of the primary reactor (varying the $H_2/C_2H_2$ ratio) is the primary process control function for maintaining target acetylene content in the feed to the secondary reactor (primary effluent). In practice the actual hydrogen demand and process restraints are as follows: (a) $H_2/C_2H_2$ ratio increases with catalyst aging; (b) $H_2/C_2H_2$ varies as carbon monoxide varies; (c) $H_2/C_2H_2$ varies as conversion of $C_2H_2$ varies (indirectly, ΔT); (d) limit $H_2/C_2H_2$ as a function of ΔT/conversion rate of acetylene in the primary reactor stage; (e) rate of hydrogen addition varies with feed flow-rate and acetylene content in the primary feed stream; and (f) increases with hydrogenation of ethylene to ethane.

In the practice of the present invention, acetylene is converted to ethylene by a catalytic hydrogenation process employing adiabatic reactors in series, with an appropriate catalyst for the reactors being palladium. This catalyst has the capability of high selectivity for the hydrogenation of acetylene to ethylene when properly conditioned and process conditions are closely controlled.

In a preferred embodiment the relatively simple calculations performed by the control system may be processed digitally by a digital computer programmed in a manner known to one skilled in the art. Alternatively, the calculations may be performed in relatively simple analog circuits constructed especially for this converter application.

While the process control description is specific for an adiabatic reactor in series; with certain minor modifications it may be adapted to isothermal reactors. In this case the control logic requires that heat of reaction must be determined by measuring the temperature differentials (ΔTs) of the heat exchangers cooling media. In this case detection of onset of thermal runaway could be less sensitive. However, reaction conditions (for any, temperature SV, etc) should be more optimized over a greater length of the catalyst bed than for an adiabatic reactor (this is especially the case for the primary reactor). In accordance with a further aspect of the invention, the process control logic may be augmented and appropriate concentrations monitored to provide a reliable measure of selectivity in the conversion reaction for use in short of longer term adjustments to the system. Measurements of ethylene balance have been found to be of limited utility, as the variability in the collected data requires considerable smoothing to correct for scatter; however acetylene concentration can be monitored with good precision, and the factor ΔT/moles acetylene converted may thus be employed as a reliable measure of selectivity in the conversion reaction, with values of 80°–100° being typical for the operations described.

What is claimed is:

1. A method of operating an acetylene converter for an ethylene plant by hydrogenating the acetylene in a two-stage reactor, having primary and secondary stages, each having therein a hydrogenation catalyst, comprising:
    (a) substantially optimizing the operation of the secondary stage of the reactor to produce a relatively low concentration of acetylene in its output effluent by maintaining the concentration of acetylene in the feed stream to the secondary stage substantially constant; and
    (b) operating the primary stage of the reactor to provide an output effluent having a substantially constant acetylene content, which is then directed as an input to the secondary stage of the reactor.

2. A method of operating an acetylene converter as claimed in claim 1, wherein the step of operating the primary stage of the reactor includes the step of adjusting the molar ratio of hydrogen to acetylene in the feed stream thereto.

3. A method of operating an acetylene converter as claimed in claim 2, wherein the step of operating the primary reactor stage includes the step of controllably adding hydrogen to the primary reactor stage feed stream through a control feed stream coupled thereto.

4. A method of operating an acetylene converter as claimed in claim 3, wherein the step of adjusting the molar ratio of hydrogen to acetylene in the feed stream to the primary reactor stage is controlled in response to feedback information from an analyzer for the primary stage effluent stream which indicates the concentration of acetylene therein and feedforward information from an analyzer for the primary stage feed stream which indicates the concentrations of hydrogen and acetylene therein.

5. A method of operating an acetylene converter as claimed in claims 1 or 4, including controlling operation of the secondary reactor stage by adjusting the molar ratio of hydrogen to acetylene in the feed stream thereto.

6. A method of operating an acetylene converter as claimed in claim 5, including the step of controlling the operation of the secondary reactor stage by selectively adding hydrogen to its feed stream through a control feed stream coupled thereto.

7. A method of operating an acetylene converter as claimed in claim 6, wherein the concentration of hydrogen in the feed stream to the secondary reactor stage is controlled in response to feedback information from an analyzer for the secondary stage effluent stream which indicates the concentration therein of acetylene, and feedforward information from an analyzer for the secondary reactor stage feed stream which indicates the concentrations of hydrogen and acetylene therein.

8. A method of operating an acetylene converter as claimed in claim 1, including the steps of sensing the temperatures of the feed stream to the primary reactor stage, the feed stream to the secondary reactor stage, and the effluent stream of the secondary reactor stage, whereby both the primary and secondary reactor stages may be monitored to detect the temperature differentials thereacross and the potential onset of a thermal runaway in either stage caused by excessive conversion of ethylene to ethane.

9. A method of operating an acetylene converter as claimed in claim 3, including the steps of measuring the concentration of carbon monoxide being directed to the primary reactor stage feed stream through the control feed stream coupled thereto, and selectively adding carbon monoxide to the primary stage control feed stream in response to said carbon monoxide measurement therein to maintain the concentration of carbon monoxide in the primary stage feed stream to provide for maximum selectivity of the catalyst.

10. A method of operating an acetylene converter as claimed in claim 1, including the steps of measuring the concentration of carbon monoxide being directed to the secondary reactor stage feed stream through the secondary control feed stream, and selectively adding carbon monoxide to the secondary stage feed stream in response to said carbon monoxide measurement therein to maintain the concentration of carbon monoxide in the secondary stage feed stream to provide for maximum selectivity of the catalyst.

11. A method of operating an acetylene converter as claimed in claim 1, including the step of passing the feed stream to the primary reactor stage through a heat exchanger to selectively control its temperature.

12. A method of operating an acetylene converter as claimed in claim 1, including the step of passing the feed stream to the secondary reactor stage through a heat exchanger to selectively control its temperature.

13. A system for operating an acetylene converter for an ethylene plant in which excessive acetylene in the ethylene plant output is hydrogenated to ethylene, comprising:
(a) a primary reactor stage, having therein a hydrogenation catalyst, for partially hydrogenating acetylene in the ethylene plant output to ethylene;
(b) a secondary reactor stage, coupled to receive the effluent from the primary reactor stage, for substantially completing the hydrogenation of acetylene to bring the acetylene concentration in the stream to within process specifications;
(c) a control means for the primary reactor stage for operating the primary reactor stage in a manner to maintain the concentration of acetylene in its effluent stream relatively constant; and
(d) a control means for the secondary reactor stage for substantially optimizing the operation of the secondary reactor stage on its feed stream having said relatively constant concentration of acetylene to produce a relatively low concentration of acetylene in the output effluent of the secondary reactor stage.

14. A system for operating an acetylene converter as claimed in claim 13, including:
(a) an analyzer means for the feed stream for the primary reactor stage for measuring the concentrations therein of hydrogen, acetylene and ethylene;
(b) an analyzer means for the feed stream for the secondary reactor stage for measuring the concentrations therein of hydrogen, acetylene and ethylene; and
(c) an analyzer means for the effluent stream of the secondary reactor stage for analyzing the concentrations therein of acetylene and ethylene.

15. A system for operating an acetylene converter as claimed in claim 14, wherein:
(a) said control means for the primary reactor stage is responsive to feedforward information from a rate-of-flow transducer for the feed stream for the primary reactor stage and also the primary stage feed stream analyzer indicating the concentrations of hydrogen and acetylene therein, and feedback information from the analyzer for the feed stream of the secondary reactor stage indicating the concentration therein of acetylene to adjust the amount of hydrogen in the feed stream of the primary reactor stage.

16. A system for operating an acetylene converter for an ethylene plant as claimed in claim 15, including a carbon monoxide analyzer for measuring the concentration of carbon monoxide in the feed stream for the primary reactor stage, and said control means for the primary reactor stage includes means, responsive to the output of said carbon monoxide analyzer, to selectively add carbon monoxide to the control feed stream for the primary reactor stage.

17. A system for operating an acetylene converter as claimed in claims 14 or 15, wherein:
(a) said control means for the secondary reactor stage is responsive to feedforward information from a rate-of-flow transducer for the feed stream for the primary reactor stage and also the secondary stage feed stream analyzer indicating the concentrations of hydrogen and acetylene therein, and feedback information from the analyzer for the effluent stream of the secondary reactor stage indicating the concentration therein of acetylene to adjust the amount of hydrogen in the feed stream of the secondary reactor stage.

18. A system for operating an acetylene converter for an ethylene plant as claimed in claim 17, including a carbon monoxide analyzer for measuring the concentration of carbon monoxide in the feed stream for the secondary reactor stage, and said control means for the secondary reactor stage includes means, responsive to the output of said secondary feed stream analyzer, to selectively add carbon monoxide to the control feed stream for the secondary reactor stage.

* * * * *